United States Patent [19]
Sato et al.

[11] Patent Number: 6,037,308
[45] Date of Patent: Mar. 14, 2000

[54] DIPHENYL SULFONE CROSSLINKING TYPE COMPOUNDS AND RECORDING MATERIALS USING THEM

[75] Inventors: Takehiro Sato, Kanagawa; Hiroshi Fujii; Shinichi Sato, both of Chiba; Izuo Aoki, Ichihara, all of Japan

[73] Assignee: Nippon Soda Co., Ltd., Tokyo, Japan

[21] Appl. No.: 09/066,461

[22] PCT Filed: Oct. 25, 1996

[86] PCT No.: PCT/JP96/03117

§ 371 Date: Apr. 30, 1998

§ 102(e) Date: Apr. 30, 1998

[87] PCT Pub. No.: WO97/16420

PCT Pub. Date: May 9, 1997

[30] Foreign Application Priority Data

| Oct. 31, 1995 | [JP] | Japan | 7-306589 |
| Mar. 5, 1996 | [JP] | Japan | 8-075304 |
| Mar. 13, 1996 | [JP] | Japan | 8-084615 |
| Mar. 22, 1996 | [JP] | Japan | 8-093318 |
| May 15, 1996 | [JP] | Japan | 8-145040 |

[51] Int. Cl.[7] ............ B41M 5/155; B41M 5/30
[52] U.S. Cl. ............ 503/216; 106/31.17; 106/31.18; 503/225; 568/32; 568/33; 568/45
[58] Field of Search ............ 106/31.17, 31.18; 503/216, 217, 225; 568/32, 33, 45

[56] References Cited

U.S. PATENT DOCUMENTS

| 4,446,209 | 5/1984 | Iwakura et al. | 503/216 |
| 5,420,094 | 5/1995 | Araki et al. | 503/216 |

FOREIGN PATENT DOCUMENTS

| 0 764 635 | 3/1997 | European Pat. Off. | 503/216 |
| 6-172299 | 6/1994 | Japan | 503/216 |
| 7-149713 | 6/1995 | Japan | 503/216 |
| WO93/06074 | 4/1993 | WIPO | 503/216 |

*Primary Examiner*—Bruce H. Hess
*Attorney, Agent, or Firm*—Jacobson, Price, Holman & Stern, PLLC

[57] ABSTRACT

Diphenyl sulfone crosslinking type compounds of general formula (1) and a recording material containing at least one of them. This recording material is excellent in the storage stability of colored images.

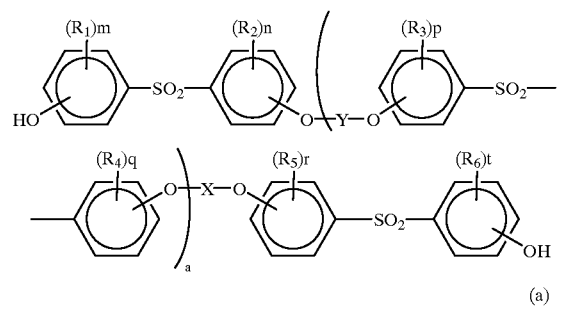

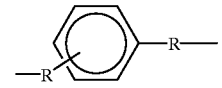

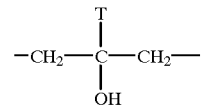

5 Claims, No Drawings

DIPHENYL SULFONE CROSSLINKING TYPE COMPOUNDS AND RECORDING MATERIALS USING THEM

FIELD OF THE INVENTION

The present invention relates to novel diphenyl sulfone crosslinking compounds and recording materials containing them with excellent image preservability.

BACKGROUND ART

Recording materials based on a color forming reactions between a coloring chromogen and a developer allow them to record by a relatively simple device in a short time without troublesome processes such as development and fixing. They are thus used widely as thermal recording paper for output recording from FAX and printers or as carbonless paper for accounting cards in order to make several copies at once. There is a demand for recording materials which can develop colors promptly, prevent a color change in the non-image area (hereinafter referred as background) and maintain the colored (recorded) images and background firmly. Furthermore, a large number of recording materials have been used in recent years in the fields where the reliability of recorded images are very important, such as labels. Required are recording materials with high preservability against plasticizers and oils contained in organic polymer materials used for packaging. Therefore effort has been made to develop various auxiliary agents such as coloring chromogens, developers and stabilizers. Fully satisfactory materials have not been found yet. Compounds having a structure of diphenyl sulfone crosslinking, which are similar to those of the present invention, are disclosed in Japanese patent laid-opened Nos. Hei 5-194368 and Hei 5-310683, as well as Japanese Patent Laid-Opened Hei 7-149713 and World opened WO93/06074 and WO95/33714. These compounds are hardly satisfactory from the viewpoint of high recorded image preservability.

Improvements in recording materials are wanted in the preservability of colored images, and particularly in recent years in resistance against plasticizers, oils, light, humidity and heat. It is an object of the present invention to provide recording materials with excellent preservability of colored images in order to solve the problems mentioned above.

DISCLOSURE OF THE INVENTION

The present invention relates to diphenyl sulfone crosslinking compounds represented by general formula (I):

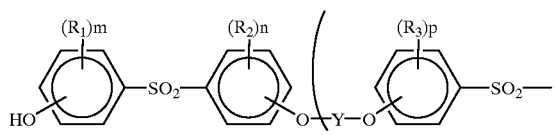

(I)

-continued

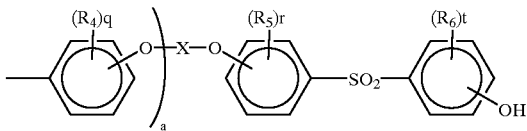

wherein X and Y are, same or different, straight-chain or branched, saturated or unsaturated $C_1$~$C_{12}$ hydrocarbon which may have an ether linkage, or

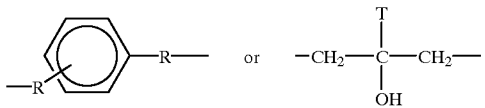

wherein

R is methylene or ethylene, T is hydrogen and an alkyl group having 1~4 carbons;

$R_1$~$R_6$ are independently halogen, an alkyl group having 1 to 6 carbons or an alkenyl group; m, n, p, q, r, t are 0 or an integer between 1 and 4 and, when more than 2, $R_1$~$R_6$ may be different each other; and a is an integer between 1~10.

Examples of groups represented by X and Y are methylene, ethylene, trimethylene, tetramethylene, pentamethylene, hexamethylene, heptamethylene, octamethylene, nonamethylene, decamethylene, undecamethylene, dodecamethylene, methylmethylene, dimethylmethylene, methylethylene, methyleneethylene, ethylethylene, 1,2-dimethylethylene, 1-methyltrimethylene, 1-methyltetramethylene, 1,3-dimethyltrimethylene, 1-ethyl-4-methyl-tetramethylene, vinylene, propenylene, 2-butenylene, ethynylene, 2-butynylene, 1-vinylethylene, ethyleneoxyethylene, tetramethyleneoxytetramethylene, ethyleneoxyethyleneoxyethylene, ethyleneoxymethyleneoxyethylene, 1,3-dioxane-5,5-bismethylene, 1,2-xylyl, 1,3-xylyl, 1,4-xylyl, 2-hydroxytrimethylene, 2-hydroxy-2-methyltrimethylene, 2-hydroxy-2-ethyltrimethylene, 2-hydroxy-2-propyltrimethylene, 2-hydroxy-2-isopropyltrimethylene and 2-hydroxy-2-butyltrimethylene. The alkyl or alkenyl groups of $R_1$~$R_6$ are $C_1$~$C_6$ alkyl or $C_2$~$C_6$ alkenyl. Their examples are methyl, ethyl, n-propyl, isopropyl, n-butyl, sec-butyl, tert-butyl, n-pentyl, isopentyl, neopentyl, tert-pentyl, n-hexyl, isohexyl, 1-methylpentyl, 2-methylpentyl, vinyl, allyl, isopropenyl, 1-propenyl, 2-butenyl, 3-butenyl, 1,3-butanedienyl and 2-methyl-2-propenyl.

Halogen is chlorine, bromine, fluorine or iodine.

It is preferable to produce the diphenyl sulfone crosslinking compounds represented by general formula (I) in water or in a bilayer solvent system consisting of water and an organic solvent, in the presence of a base compound. They may be produced according to the following reaction schemes. Preferred starting materials are 4,4'-dihydroxydiphenyl sulfone derivatives or 2,4'-dihydroxydiphenyl sulfone derivatives due to easy availability.

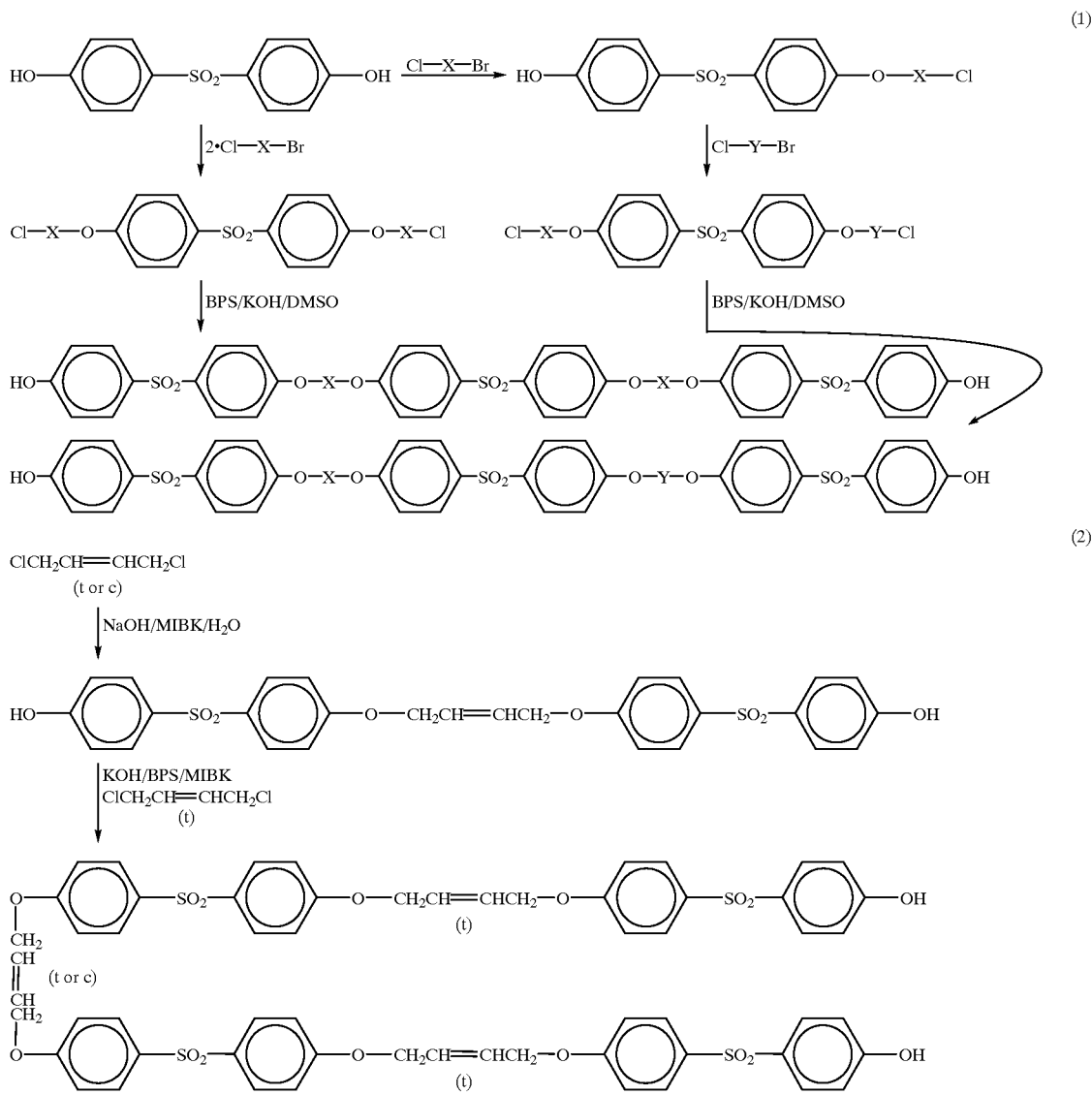

In the bilayer system of water and an organic solvent, a reaction is carried out in a water-insoluble organic solvent including a benzene-type organic solvent such as benzene, toluene, chlorobenzene and dichlorobenzene; ketone-type organic solvent such as diethylketone and methylisobutylketone (MIBK) and ester organic solvent such as ethyl acetate, in the presence of an alkaline compound including a hydroxide of alkali metal or alkaline earth metal such as sodium hydroxide, potassium hydroxide or lithium hydroxide, at the reaction temperature between −20° C.~150° C., preferably 30° C.~120° C. for several hours to 10-odd hours. A reaction in water is carried out in water in the presence of an alkaline compound mentioned above at the reaction temperature between 0° C.~120° C. for several hours to 10-odd hours.

After the reaction, selective extraction with solvents gives a single compound with high purity.

Butenyloxy compounds can be obtained by reacting 4,4'-dihydroxydiphenyl sulfone (BPS) with, for example, a 1,4-dihalobutene in the presence of a hydroxide of alkali metal or alkaline earth metal (such as sodium hydroxide, potassium hydroxide or lithium hydroxide) or their carbonate (such as sodium carbonate, potassium carbonate or lithium carbonate) in an aromatic solvent such as toluene, xylene or chlorobenzene or ketone solvent such as acetone or MIBK, or in a bilayer system with an organic solvent mentioned above and water.

Alkylene crosslinking compounds can be obtained by reacting, for example, BPS with, for example, 1-bromo-4-chlorobutane in the presence of a hydroxide of alkali metal or alkaline earth metal (such as sodium hydroxide, potassium hydroxide or lithium hydroxide) or their carbonate (such as sodium carbonate, potassium carbonate or lithium carbonate) in an aromatic solvent such as toluene, xylene or chlorobenzene or ketone solvent such as acetone or MIBK, or in a bilayer system with an organic solvent mentioned above and water, then reacting the obtained product with BPS in the presence of an alkali metal, alkaline earth metal or their carbonate in a solvent such as dimethylsulfoxide (DMSO), dimethylformamide (DMF) or MIBK.

The present invention also relates to composites containing at least one of diphenyl sulfone crosslinking compounds represented by

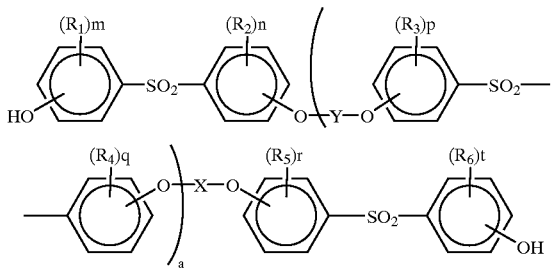

wherein X, Y, $R_1$~$R_6$, m, n, p, q, r, t and a are as defined above, and at least one of diphenyl sulfone derivatives represented by general formula (II)

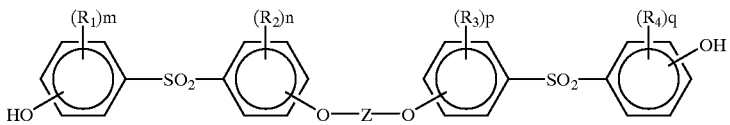

wherein $R_1$~$R_4$, m, n, p and q are as defined above and Z is a straight-chain or branched, saturated or unsaturated $C_1$~$C_{12}$ hydrocarbon group which may have an ether linkage, or

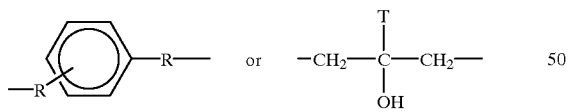

wherein R is methylene or ethylene and T is hydrogen or an alkyl group of 1 to 4 carbons.

The essential components of the composites in accordance with the present invention are at least one of the diphenyl sulfone crosslinking compounds represented by general formula (I) and at least one of the diphenyl sulfone derivatives represented by general formula (II). Their ratio is determined arbitrarily. The diphenyl sulfone crosslinking compound represented by general formula (I) is preferably 0.05~99% by weight, more preferably 1~90% by weight and most preferably 5~80% by weight. When two or more compounds of general formula (I) are contained, their total is the percent by weight mentioned above.

The compounds of general formula (I) and the derivatives of general formula (II) may be contained in a composite of this invention by mixing in the form of powder, mixing by melting, adding compounds of general formula (I) or derivatives of general formula (II) when they are crystallized after synthesis, or producing the compounds and the derivatives concurrently by changing production conditions of one of them. Particularly preferred composites are those containing two or more compounds which have only a different value of b of the compounds represented by general formula (III). In this case, b=1~10 for the diphenyl sulfone crosslinking compounds represented by general formula (I) of this invention and b=0 for the diphenyl sulfone derivative represented by general formula (II).

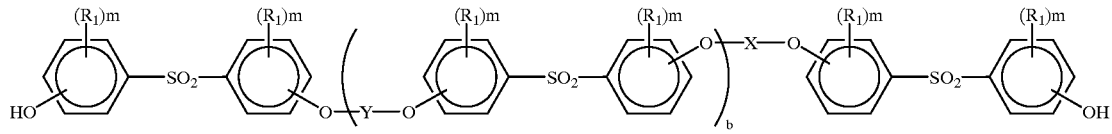

Wherein X, $R_1$ and m are as defined above.

The production process for the above case is simple. Changing a ratio of starting materials for the reaction arbitrarily changes the ratio of the diphenyl sulfone crosslinking compounds represented by general formula (I) and diphenyl sulfone derivatives represented by general formula (II) in a composite.

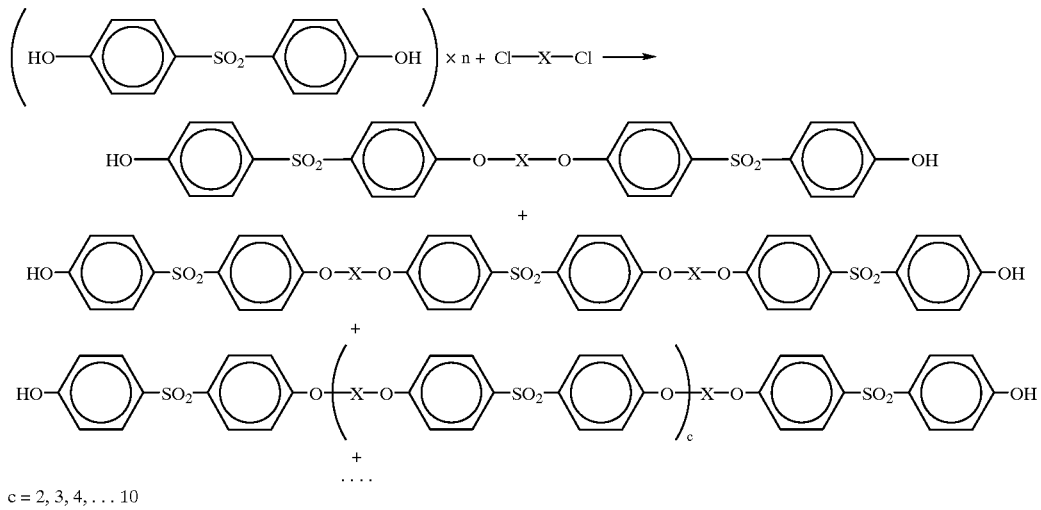

c = 2, 3, 4, ... 10

The compounds represented by general formula (II), which are used in the present invention, are those disclosed in Japanese Patent Laid-Opened No. Hei 7-149713, World opened W093/06074 and W095/33714. Representative examples are:

1,3-bis[4-(4-hydroxyphenylsulfonyl)phenoxy]-2-hydroxypropane
1,1-bis[4-(4-hydroxyphenylsulfonyl)phenoxy]methane
1,2-bis[4-(4-hydroxyphenylsulfonyl)phenoxy]ethane
1,3-bis[4-(4-hydroxyphenylsulfonyl)phenoxy]propane
1,4-bis[4-(4-hydroxyphenylsulfonyl)phenoxy]butane
1,5-bis[4-(4-hydroxyphenylsulfonyl)phenoxy]pentane
1,6-bis[4-(4-hydroxyphenylsulfonyl)phenoxy]hexane
α,α'-bis[4-(4-hydroxyphenylsulfonyl)phenoxy]-p-xylene
α,α'-bis[4-(4-hydroxyphenylsulfonyl)phenoxy]-m-xylene
α,α'-bis[4-(4-hydroxyphenylsulfonyl)phenoxy]-o-xylene
2,2'-bis[4-(4-hydroxyphenylsulfonyl)phenoxy]diethyl ether
4,4'-bis[4-(4-hydroxyphenylsulfonyl)phenoxy]dibutyl ether
1,2-bis[4-(4-hydroxyphenylsulfonyl)phenoxy]ethylene
1,4-bis[4-(4-hydroxyphenylsulfonyl)phenoxy]-2-butene.

BEST MODE FOR CARRYING OUT THE INVENTION

The present invention is further described in detail with examples, but is not restricted to them. Some compounds of general formula (I) have isomers when they have a double bond. These are also covered by the present invention.

The compounds of the present invention may be different in crystal form, be amorphous or form an adduct with a solvent, depending on crystallization conditions, for example, solvents used and crystallization temperature. These compounds can be defined by the melting point of the crystal, infrared spectroscopy or X-ray diffraction analysis and are covered by the present invention.

EXAMPLE 1

Synthesis of 4,4'-bis[4-[4-(4-hydroxyphenylsulfonyl)phenoxy]-2-trans-butenyloxy]diphenyl sulfone [Compound (1-1)]

Into a 300-ml, 4-neck flask were placed 5 g of trans-1,4-dichlorobutene, 20 g of 4,4'-dihydroxy-diphenylsulfone (hereinafter abbreviated as BPS) and 3.2 g of sodium hydroxide. Then 150 ml of methyl isobutyl ketone (hereinafter abbreviated as MIBK) and 100 ml of water were further added. The resulting solution was heated at reflux for 3 hours. After the reaction was completed, the MIBK layer was washed with a 1% aqueous solution of sodium hydroxide in order to remove unreacted BPS. The MIBK layer was concentrated to give crude crystals. The obtained crystals were heated in methanol at reflux and filtrated hot to obtain insoluble matter. The resulting product was further heated in methanol at reflux and purified by filtrating hot to give 1.5 g of Compound (1-1). Melting point (°C.): 176~180. Yield: 5%.

EXAMPLE 2

Synthesis of 4,4'-bis[4-(4-hydroxyphenylsulfonyl) phenoxy-3-propyloxy]diphenyl sulfone [Compound (1-3)]

Into a 300-ml, 4-neck flask were placed 12.5 g of BPS, 4.3 g of sodium hydroxide and 15.7 g of 1-bromo-3-chloropropane. Further 150 ml of MIBK was added to heat at reflux for 12 hours. After the reaction was completed, the MIBK layer was washed with a 1% aqueous solution of sodium hydroxide in order to remove unreacted BPS. MIBK was distilled under reduced pressure to give an oily reaction product of 4,4-bis(3-chloropropyloxy) diphenyl sulfone (crystallized from toluene/hexane, melting point of 70~73° C.). 5 g of the obtained product and 5 g of BPS were dissolved in 30 ml of DMSO and 1.5 g of sodium hydroxide was added. The resulting solution was reacted for 6 hours at 100° C. After the reaction was completed, the precipitated crystals were filtrated and washed with water and acetonitrile in this order to give 4 g of Compound (1-3). Melting point (°C.): 237~242. Yield: 40%.

EXAMPLE 3

Synthesis of 4,4'-bis[4-(4-hydroxyphenylsulfonyl) phenoxy-2-ethyleneoxyethoxy]diphenyl sulfone [Compound (1-17)]

10.0 g (29 mmol) of 4-benzyloxy-4'-hydroxydiphenyl sulfone was dissolved in 50 ml of N,N-dimethylformamide (hereinafter abbreviated as DMF). To the obtained solution were added 3.9 g (29 mmol) of tert-butoxy potassium at 10° C. and 8.4 g (58 mmol) of bis(2-chloroethyl) ether at room temperature. The resulting solution was reacted at 90° C. for 6 hours, poured into 200 ml of water and extracted with 200 ml of MIBK. The organic layer was washed with a 1% aqueous solution of sodium hydroxide and water, then concentrated. The obtained oil was purified through a column to give 8.0 g of white crystals of 4-benzyloxy-4'-(2-chloroethoxy)ethoxydiphenyl sulfone. The yield from bis(2-chloroethyl) ether was 61%.

2.0 g (8 mmol) of BPS was dissolved in 40 ml of DMF. To the obtained solution were added 1.8 g (16 mmol) of tert-butoxy potassium at 10° C. and 8.0 g (17.6 mmol) of 4-benzyloxy-4'-(2-chloroethoxy) ethoxydiphenyl sulfone at room temperature. The resulting solution was reacted at 100° C. for 8 hours. After the reaction was completed, 100 ml of water was added to the reaction solution, then 6N hydrochloric acid to adjust the pH to 5. The precipitated crystals were filtrated and purified by recrystallization from acetic acid to give 6.3 g of white crystals of 4,4'-bis[4-(4-benzyloxyphenylsulfonyl)phenoxy-2-ethyleneoxyethoxy]diphenyl sulfone. The yield from 4-benzyloxy-4'-(2-chloroethoxy)ethoxydiphenyl sulfone was 73%.

50 ml of acetic acid was added to 3.0 g (2.8 mmol) of the obtained crystals, then 2.0 g (11.2 mmol) of 47% hydrobromic acid. The resulting solution was reacted at 110° C. for 3 hours, cooled down to room temperature after the reaction was completed and filtrated. The obtained crude crystals were recrystallized from acetone to give 1.5 g of white crystals of the titled compound having melting point :130~134° C., 4,4'-bis[4-(4-hydroxyphenylsulfonyl)phenoxy-2-ethyleneoxyethoxy]diphenyl sulfone. The structure was confirmed by $^1$H-NMR. The purity measured by high performance liquid chromatography was 96.1%. The yield from 4,4'-bis[4-(4-benzyloxyphenylsulfonyl)phenoxy-2-ethyleneoxyethoxy]diphenyl sulfone was 60%.

REFERENCE EXAMPLE 1

Synthesis of 2,2'-bis[4-(4-hydroxyphenylsulfonyl) phenoxy]diethyl ether 64.0 g (1.60 mol) of sodium hydroxide was dissolved in 84.0 g of water and 200.0 g (0.80 mol) of BPS was added. Then 14.3 g (0.10 mol) of bis(2-chloroethyl) ether was added at 100° C. The resulting solution was reacted at 100° C.~110° C. for 5 hours. After the reaction was completed, 1300 ml of water was added to the reaction solution, cooled down to room temperature and filtrated with radiolyte. 1300 ml of methanol was added to the filtrate. The resulting solution was neutralized with 95% sulfuric acid. The precipitated crystals were filtrated, washed with 1000 ml of water, then with 250 ml of methanol to give 34.2 g of white crystals of the titled compound of 2,2'-bis[4-(4-hydroxyphenylsulfonyl)phenoxy]diethyl ether with melting point of 171~172° C. The structure was confirmed by $^1$H-NMR. The purity measured by high performance liquid chromatography was 98.7%. The yield from bis(2-chloroethyl) ether was 60%.

EXAMPLE 4

Compound (2-1)

18.0 g of white crystals of 2,2'-bis[4-(4-hydroxyphenylsulfonyl) phenoxy]diethyl ether and 2.0 g of white crystals of 4,4'-bis[4-(4-hydroxyphenylsulfonyl)phenoxy-2-ethyleneoxyethoxy]diphenyl sulfone were ground well in a mortar to mix them. The purity of the mixture measured by high performance liquid chromatography was 88.8% for 2,2'-bis[4-(4-hydroxyphenylsulfonyl) phenoxy]diethyl ether and 9.61% for 4,4'-bis[4-(4-hydroxyphenylsulfonyl)phenoxy-2-ethyleneoxyethoxy]diphenyl sulfone.

EXAMPLE 5

Compound (2-5)

96.0 g (2.4 mol) of sodium hydroxide was dissolved in 126.0 g of water and 300.0 g (1.2 mol) of BPS was added. Then, at 105° C., 42.9 g (0.30 mol) of bis(2-chloroethyl) ether was added. The resulting solution was reacted at 110° C.~115° C. for 3 hours. After the reaction was completed, 1500 ml of water was added to the reaction solution. 50% sulfuric acid was added at 20° C. to adjust the pH to 9.0. The precipitated crystals were filtrated, washed with 100 ml of water and dried to give 138 g of white amorphous product with melting point of 75~81° C. and containing 2,2'-bis[4-(4-hydroxyphenylsulfonyl)phenoxy]diethyl ether. The purity measured by high performance liquid chromatography was 67.7%. In addition to the above compound, the amorphous contained 23.1% of 4,4'-bis[4-(4-hydroxyphenylsulfonyl)phenoxy- 2-ethyleneoxyethoxy]diphenyl sulfone and 5.5% of 2,2-bis[4-[4-[4-(4-hydroxyphenylsulfonyl)phenoxy-2-ethyleneoxyethoxy]phenylsulfonyl]phenoxy]diethyl ether. The yield from bis(2-chloroethyl) ether was 80.7%.

A reaction was repeated as mentioned above. After the reaction was completed, 1500 ml of water was added to the reaction solution, followed by the addition of 50% of sulfuric acid at 20° C. to adjust the pH to 9.0. The precipitated crystals were filtrated and washed with 1000 ml of water. The crystals were kept in 1000 ml of a 50% aqueous methanol solution at 70° C. for an hour, then cooled down to room temperature. The crystals were filtrated, washed with a 50% aqueous methanol solution and dried to give 135 g of white crystals with melting point of 130~145° C. and containing 2,2'-bis[4-(4-hydroxyphenylsulfonyl)phenoxy]diethyl ether. The purity measured by high performance liquid chromatography was 69.4%. In addition to the above compound, the crystals contained 23.3% of 4,4'-bis[4-(4-hydroxyphenylsulfonyl)phenoxy-2-ethyleneoxyethoxy]diphenyl sulfone and 5.5% of 2,2-bis[4-[4-[4-(4-hydroxyphenylsulfonyl)phenoxy-2-ethyleneoxyethoxy]phenylsulfonyl]phenoxy]diethyl ether. The yield from bis(2-chloroethyl) ether was 79.1%.

EXAMPLE 6

16.0 g (0.4 mol) of sodium hydroxide was dissolved in 21.2 g of water and 50.0 g (0.2 mol) of BPS was added, followed by the addition of 14.3 g (0.10 mol) of bis(2-chloroethyl) ether at 105° C. The resulting solution was reacted at 110° C.~115° C. for 5 hours. After the reaction was completed, 375 ml of water was added to the reaction solution and stirred at 90° C. for an hour. After cooling down to room temperature, the solution was neutralized with 20% sulfuric acid. The precipitated crystals were filtrated to give 39.3 g of white crystals. The yield from bis(2-chloroethyl) ether was 88%.

It was analyzed by high performance liquid chromatography with a column of Mightysil RP-18 (Kanto Kagaku Co.) and the transfer phase of $CH_3CN:H_2O:1\%\ H_3PO_4$= 700:300:5 at the UV wave length of 260 nm. Its composition was as follows:

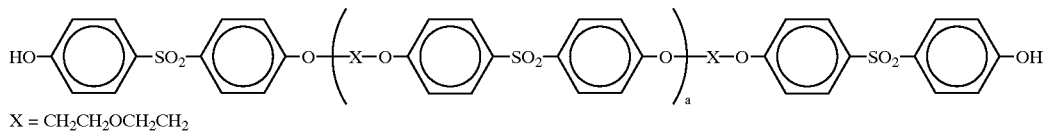

X = CH$_2$CH$_2$OCH$_2$CH$_2$

| | | |
|---|---|---|
| a = 0: | retention time 1.9 minutes: | area % 32.9 |
| a = 1: | retention time 2.3 minutes: | area % 21.7 |
| a = 2: | retention time 2.7 minutes: | area % 12.8 |
| a = 3: | retention time 3.4 minutes: | area % 8.8 |
| a = 4: | retention time 4.2 minutes: | area % 5.8 |
| a = 5: | retention time 5.4 minutes: | area % 3.5 |
| a = 6: | retention time 7.0 minutes: | area % 2.2 |
| a = 7: | retention time 9.0 minutes: | area % 1.7 |
| a = 8: | retention time 11.8 minutes: | area % 1.3 |
| a = 9: | retention time 15.4 minutes: | area % 1.3 |

EXAMPLES 7~9

Example 6 was repeated except changing a molar ratio of reacting BPS and bis(2-chloroethyl) ether to 1.5:1, 2.5:1 and 3:1. The obtained composites were as follows:

| When | | | | | |
|---|---|---|---|---|---|
| 1.5:1 a = 0 | 20.8, a = 1 | 33.0, a = 2 | 14.2, a = 3 | 7.9, a = 4 | 3.9 |
| When | | | | | |
| 2.5:1 a = 0 | 49.6, a = 1 | 25.9, a = 2 | 11.4, a = 3 | 5.3, a = 4 | 2.4 |
| When | | | | | |
| 3.0:1 a = 0 | 56.9, a = 1 | 24.9, a = 2 | 9.6, a = 3 | 3.7, a = 4 | 1.3 |

EXAMPLE 10

Compound 2-6

30.0 g (0.12 mol) of BPS was added to a mixed solution of 10.0 g of 48% aqueous solution of sodium hydroxide and 155 g of N,N'-dimethylacetamide. After raising the temperature to 80° C. to dissolve BPS, 10.5 g (0.06 mol) of α,α'-dichloro-p-xylene dissolved in 15 g of xylene was dropped slowly. After the completion of the dropping, a reaction was carried out for 2 hours at the same temperature for maturing. The reaction solution was poured into 900 ml of water. The precipitated crystals were filtrated. The obtained crude crystals were washed with methanol, filtrated and dried to give 19.7 g of white crystals. The purity was analyzed by high performance liquid chromatography. The main components were α,α'-bis[4-(4-hydroxyphenylsulfonyl)phenoxy]-p-xylene: 59.1%

4,4'-bis[4-(4-hydroxyphenylsulfonyl)phenyl-1,4-phenylenebismethyleneoxy]diphenyl sulfone: 23.1%

α,α'-bis[4-[4-(4-hydroxyphenylsulfonyl)phenyl-1,4-phenylenebismethyleneoxy]phenylsulfonyl]phenoxy]-p-xylene: 11.1%

Compounds represented by general formula (I), including those described in the examples, are exemplified below:

(1-1) 4,4'-bis[4-[4-(4-hydroxyphenylsulfonyl)phenoxy]-2-trans-butenyloxy]diphenyl sulfone: Melting point (°C.) 176~180

(1-2) 4,4'-bis[4-(4-hydroxyphenylsulfonyl)phenoxy-4-butyloxy]diphenyl sulfone: Melting point (°C.) 215~220

(1-3) 4,4'-bis[4-(4-hydroxyphenylsulfonyl)phenoxy-3-propyloxy]diphenyl sulfone: Melting point (°C.) 237~242

(1-4) 4,4'-bis[4-(4-hydroxyphenylsulfonyl)phenoxy-2-ethyloxy]diphenyl sulfone (1-5) 4-[4-(4-hydroxyphenylsulfonyl)phenoxy-4-butyloxy]-4'-[4-(4-hydroxyphenylsulfonyl)phenoxy-3-propyloxy]diphenyl sulfone (1-6) 4-[4-(4-hydroxyphenylsulfonyl)phenoxy-4-butyloxy]-4'-[4-(4-hydroxyphenylsulfonyl)phenoxy-2-ethyloxy]diphenyl sulfone (1-7) 4-[4-(4-hydroxyphenylsulfonyl)phenoxy-3-propyloxy]-4'-[4-(4-hydroxyphenylsulfonyl)phenoxy-2-ethyloxy]diphenyl sulfone (1-8) 4,4'-bis[4-(4-hydroxyphenylsulfonyl)phenoxy-5-pentyloxy]diphenyl sulfone (1-9) 4,4'-bis[4-(4-hydroxyphenylsulfonyl)phenoxy-6-hexyloxy]diphenyl sulfone: Melting point (°C.) 133~136

(1-10) 4-[4-[4-(4-hydroxyphenylsulfonyl)phenoxy]-2-trans-butenyloxy]-4'-[4-(4-hydroxyphenylsulfonyl)phenoxy-4-butyloxy]diphenyl sulfone (1-11) 4-[4-(4-hydroxyphenylsulfonyl)phenoxy-2-trans-butenyloxy]-4'-[4-(4-hydroxyphenylsulfonyl)phenoxy-3-propyloxy]diphenyl sulfone (1-12) 4-[4-[4-(4-hydroxyphenylsulfonyl)phenoxy]-2-trans-butenyloxy]-4'-[4-(4-hydroxyphenylsulfonyl)phenoxy-2-ethyloxy]diphenyl sulfone (1-13) 1,4-bis[4-[4-[4-(4-hydroxyphenylsulfonyl)phenoxy-2-trans-butenyloxy]phenylsulfonyl]phenoxy]-cis-2-butene: Melting point (°C.) 185~190

(1-14) 1,4-bis[4-[4-[4-(4-hydroxyphenylsulfonyl)phenoxy-2-trans-butenyloxy]phenylsulfonyl]phenoxy]-trans-2-butene: Melting point (°C.) 240~243

(1-15) 4,4'-bis[4-[4-(2-hydroxyphenylsulfonyl)phenoxy]butyloxy]diphenyl sulfone (1-16) 4,4'-bis[4-[2-(4-hydroxyphenylsulfonyl)phenoxy]butyloxy]diphenyl sulfone (1-17) 4,4'-bis[4-(4-hydroxyphenylsulfonyl)phenoxy-2-ethyleneoxyethoxy]diphenyl sulfone: Melting point (°C.) 130~134

(1-18) 4,4'-bis[4-(4-hydroxyphenylsulfonyl)phenyl-1,4-phenylenebismethyleneoxy]diphenyl sulfone: Melting point (°C.) 148~152

(1-19) 4,4'-bis[4-(4-hydroxyphenylsulfonyl)phenyl-1,3-phenylenebismethyleneoxy]diphenyl sulfone (1-20) 4,4'-bis[4-(4-hydroxyphenylsulfonyl)phenyl-1,2-phenylenebismethyleneoxy]diphenyl sulfone: Melting point (°C.) 224~227

(1-21) 2,2'-bis[4-[4-[4-(4-hydroxyphenylsulfonyl)phenoxy-2-ethyleneoxyethoxy]phenylsulfonyl]phenoxy]diethyl ether (1-22) α,α'-bis[4-[4-[4-(4-hydroxyphenylsulfonyl)phenyl-1,4-phenylenebismethyleneoxy]phenylsulfonyl]phenoxy]-p-xylene (1-23) α,α'-bis[4-[4-[4-(4-hydroxyphenylsulfonyl)phenyl-1,3-phenyleneismethyleneoxy]phenylsulfonyl]phenoxy]-m-xylene (1-24) α,α'-bis[4-[4-[4-(4-hydroxyphenylsulfonyl)phenyl-1,2-phenylenebismethyleneoxy]phenylsulfonyl]phenoxy]-o-xylene (1-25) 2,4'-bis[2-(4-hydroxyphenylsulfonyl)phenoxy-2-ethyleneoxyethoxy]diphenyl sulfone (1-26) 2,4'-bis[4-(2-hydroxyphenylsulfonyl)phenoxy-2-ethyleneoxyethoxy]diphenyl sulfone (1-27) 4,4'-bis[3,5-dimethyl-4-(3,5-dimethyl-4-hydroxyphenylsulfonyl)phenoxy-2-ethyleneoxyethoxy]diphenyl sulfone (1-28) 4,4'-bis[3-allyl-4-(3-allyl-4-hydroxyphenylsulfonyl)phenoxy-2-ethyleneoxyethoxy]diphenyl sulfone (1-29) 4,4'-bis[3,5-dimethyl-4-(3,5-dimethyl-4-hydroxyphenylsulfonyl)phenyl-1,4-phenylenebismethyleneoxy]diphenyl sulfone (1-30) 4,4'-bis[3,5-dimethyl-4-(3,5-dimethyl-4-hydroxyphenylsulfonyl)phenyl-1,3-phenylenebismethyleneoxy]diphenyl sulfone (1-31) 4,4'-bis[3,5-dimethyl-4-(3,5-dimethyl-4-hydroxyphenylsulfonyl)phenyl-1,2-phenylenebismethyleneoxy]diphenyl sulfone (1-32) 4,4'-bis[3-allyl-4-(3-allyl-4-hydroxyphenylsulfonyl)-1,4-phenylenebismethyleneoxy]diphenyl sulfone (1-33) 4,4'-bis[3-allyl-4-(3-allyl-4-hydroxyphenylsulfonyl)-1,3-phenylenebismethyleneoxy]diphenyl sulfone (1-34) 4,4'-bis[3-allyl-4-(3-allyl-4-hydroxyphenylsulfonyl)-1,2-phenylenebismethyleneoxy]diphenyl sulfone (1-35) 4,4'-bis[4-(4-hydroxyphenylsulfonyl)phenoxy-2-hydroxypropyloxy]diphenyl sulfone (1-36) 1,3-bis[4-[4-[4-(4-hydroxyphenylsulfonyl)phenoxy-2-hydroxypropyloxy]phenylsulfonyl]phenoxy]-2-hydroxypropane Examples of combinations of compounds of the general formulae (I) and (II) for composites are described below, including those in the examples.

(2-1) Combination of 2,2'-bis[4-(4-hydroxyphenylsulfonyl)phenoxy]diethyl ether and 4,4'-bis[4-(4-hydroxyphenylsulfonyl)phenoxy-2-ethyleneoxyethoxy]diphenyl sulfone (2-2) Combination of α,α'-bis[4-(4-hydroxyphenylsulfonyl)phenoxy-p-xylene and 4,4'-bis[4-(4-hydroxyphenylsulfonyl)phenyl-1,4-phenylenebismethyleneoxy]diphenyl sulfone (2-3) Combination of α,α'-bis[4-(4-hydroxyphenylsulfonyl)phenoxy-m-xylene and 4,4'-bis[4-(4-hydroxyphenylsulfonyl)phenyl-1,3-phenylenebismethyleneoxy]diphenyl sulfone (2-4) Combination of α,α'-bis[4-(4-hydroxyphenylsulfonyl)phenoxy-o-xylene and 4,4'-bis[4-(4-hydroxyphenylsulfonyl)phenyl-1,2-phenylenebismethyleneoxy]diphenyl sulfone (2-5) Combination of 2,2'-bis[4-(4-hydroxyphenylsulfonyl)phenoxy]diethyl ether and 4,4'-bis[4-(4-hydroxyphenylsulfonyl)phenoxy-2-ethyleneoxyethoxy]diphenyl sulfone and 2,2'-bis[4-[4-[4-(4-hydroxyphenylsulfonyl)phenoxy-2-ethyleneoxyethoxy]phenylsulfonyl]phenoxy]diethyl ether (2-6) Combination of α,α'-bis[4-(4-hydroxyphenylsulfonyl)phenoxy-p-xylene and 4,4'-bis[4-(4-hydroxyphenylsulfonyl)phenyl-1,4-phenylenebismethyleneoxy]diphenyl sulfone and α,α'-bis[4-[4-[4-(4-hydroxyphenylsulfonyl)phenyl-1,4-phenylenebismethyleneoxy]phenylsulfonyl]phenoxy]-p-xylene (2-7) Combination of α,α'-bis[4-(4-hydroxyphenylsulfonyl)phenoxy-m-xylene and 4,4'-bis[4-(4-hydroxyphenylsulfonyl)phenyl-1,3-phenylenebismethyleneoxy]diphenyl sulfone and α,α'-bis[4-[4-[4-(4-hydroxyphenylsulfonyl)phenyl-1,3-phenylenebismethyleneoxy]phenylsulfonyl]phenoxy]-m-xylene (2-8) Combination of α,α'-bis[4-(4-hydroxyphenylsulfonyl)phenoxy-o-xylene and 4,4'-bis[4-(4-hydroxyphenylsulfonyl)phenyl-1,2-phenylenebismethyleneoxy]diphenyl sulfone and α,α'-bis[4-[4-[4-(4-hydroxyphenylsulfonyl)phenyl-1,2-phenylenebismethyleneoxy]phenylsulfonyl]phenoxy]-o-xylene (2-9) Combination of 1,4-bis[4-(4-hydroxyphenylsulfonyl)phenoxy]-trans-2-butene and 4,4'-bis[4-(4-hydroxyphenylsulfonyl)phenoxy-2-trans-butenyloxy]diphenyl sulfone (2-10) Combination of 1,2-bis[4-(4-hydroxyphenylsulfonyl)phenoxy]-ethane and 4,4'-bis[2-(4-hydroxyphenylsulfonyl)phenoxy-ethyloxy]diphenyl sulfone (2-11) Combination of 1,4-bis[4-(4-hydroxyphenylsulfonyl)phenoxy]-butane and 4,4'-bis[4-(4-hydroxyphenylsulfonyl)phenoxy-butyloxy]diphenyl sulfone (2-12) Combination of 1,6-bis[4-(4-hydroxyphenylsulfonyl)phenoxy]hexane and 4,4'-bis[6-(4-hydroxyphenylsulfonyl)phenoxy-hexyloxy]diphenyl sulfone (2-13) Combination of 1,3-bis[4-(4-hydroxyphenylsulfonyl)phenoxy]-2-hydroxypropane and 4,4'-bis[4-(4-hydroxyphenylsulfonyl)phenoxy-2-hydroxypropyloxy]diphenyl sulfone (2-14) Combination of 1,3-bis[4-(4-hydroxyphenylsulfonyl)phenoxy]-2-hydroxypropane and 4,4'-bis[4-(4-hydroxyphenylsulfonyl)phenoxy-2-hydroxypropyloxy]diphenyl sulfone and 1,3-bis[4-[4-(4-hydroxyphenylsulfonyl)phenoxy-2-hydroxypropyloxy]phenylsulfonyl]phenoxy]-2-hydroxypropane The present invention relates to recording materials containing coloring chromogens, in which at least one of the diphenyl sulfone crosslinking compounds represented by general formula (I)

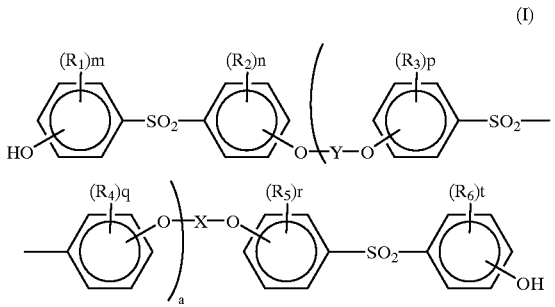

wherein X, Y, $R_1$~$R_6$, m, n, p, q, r, t and a are as described above, is used.

The compounds of this invention can be used for any purposes if they are used for recording materials using coloring chromogens, for example for thermal recording materials and carbonless papers.

Remarkable points of the compounds of this invention are that recording materials with excellent plasticizer resistance can be produced when they contain at least one of the diphenyl sulfone crosslinking compounds represented by general formula (I) and that the compounds can be used as developers or image stabilizing agents.

Recording materials containing coloring chromogens can be produced by general methods known in the art. For example, the compounds of this invention may be used together with other developers and various auxiliary agents such as sensitizers in case that they are used as image stabilizing agents. When used as developers, they can be used together with various auxiliary agents such as sensitizers in order to produce recording materials. It is possible to use in combination of compounds of this invention, one of them as an image stabilizing agent and another as a developer. It is also possible to produce recording materials characteristic in coloring by the combined use of the compounds of this invention and other compounds with the same application.

As described above, the compounds of the present invention have two ways of use, that is, as image stabilizing agents and developers. It is advantageous that a required amount of an image stabilizing agent and a developer, relative to that of a coloring chromogen, can be thus reduced for each other so as to produce inexpensive recording materials.

The compounds of this invention, when used for carbonless paper, can be used in a similar manner to that of known image stabilizing agents and developers. For example, fine particles of a compound of this invention and a coloring chromogen are separately dispersed in an aqueous solution of water-soluble binder such as polyvinyl alcohol or cellulose. These suspensions are mixed to apply onto a support such as paper and dried to produce carbonless paper.

A ratio of a compound of this invention to a coloring chromogen is 0.1~5 parts by weight to a part by weight of the coloring chromogen, preferably 0.2~2 parts by weight, when the compound is used as an image stabilizer. When used as a developer, a ratio is 1~10 parts by weight, preferably 1.5~5 parts by weight, to a part by weight of the chromogen.

A combined use of a compound represented by general formula (I) and a compound represented by general formula (II) is very effective.

The present invention also relates to recording materials containing at least one of diphenyl sulfone crosslinking compounds represented by general formula (I) at least one of the compounds of general formula (I) is used together with at least one of the compounds of general formula (II) for recording materials. In this case a compound represented by general formula (I) and one represented by general formula (II) can be used in an ordinary relation between a developer and an image stabilizing agent. The effect is outstandingly improved even if an additional amount of a compound of general formula (I) is added to a compound of general formula (II).

A mixing ratio by weight of a compound represented by general formula (I) and one represented by general formula (II) is I:II=0.05:100~99:1, preferably 1:99~90:10 and more preferably 5:95~80:20. When high preservability is required, the ratio is preferably 50:50~80:20. It is preferably 5:95~50:50 when high sensitivity is required.

When two or more compounds of each of those represented by the general formulae (I) and (II) are used, the values of the above ratios by weight are the total weight of respective compounds.

Compounds represented by the general formulae (I) and (II) may be mixed in the form of powder, by adding when a coating liquid is prepared and dispersed, or by adding in the form of dispersion. A composite containing both compounds represented by general formulae (I) and (II) can be used depending on the selection of a manufacturing method of the compounds. It is extremely effective when a composite containing at least one of the diphenyl sulfone crosslinking compounds of general formula (I) and diphenyl sulfone derivatives of general formula (II) is used as a developer.

The compounds and composites of this invention, as mentioned above, cover the same compound but different in the degree of crystallinity or crystal form, amorphous compounds and solvent adducts. The use of these compounds may improve the ground and sensitivity of recording mate-

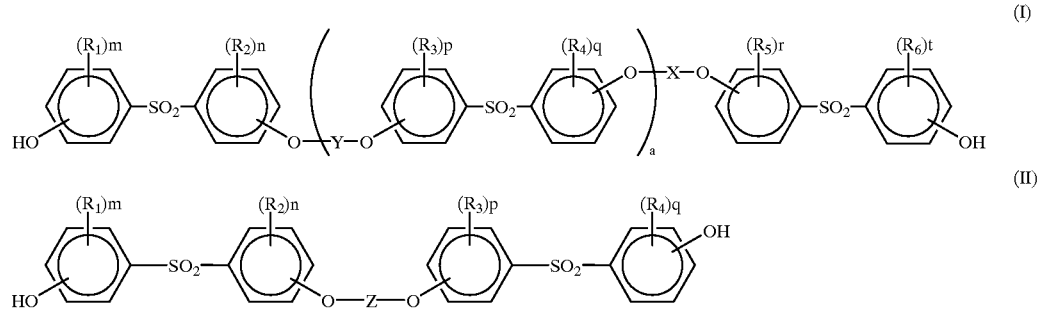

wherein $R_1$~$R_4$, m, n, p and q are as defined above and Z is straight-chain or branched, saturated or unsaturated $C_1$~$C_{12}$ hydrocarbon which may have an ether linkage, or

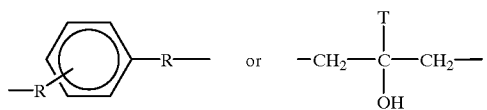

wherein R is methylene or ethylene, T is hydrogen or an alkyl group of 1 to 4 carbons.

Recording materials containing a compound represented by general formula (II) have been disclosed in Japanese Patent Laid-Open No Hei 7-149713 and World Patents opened Nos. W093/06074 and W095/33714. The disclosed compounds endow excellent plasticizer resistance to recording materials when used in the similar manner to that of the compounds represented by general formula (I). However, their effect is not satisfactory yet. It is more effective when rials. The sensitivity may be improved if fine particles of these compounds are used in the coating solution. Particularly compounds with a high degree of crystallinity give better whiteness and heat resistance of the ground to the recording materials than amorphous ones.

To the dispersions mentioned above may be added, if required, other developers, other image stabilizing agents, sensitizers, fillers, dispersing agents, antioxidants, desensitizers, antitack agents, defoamers, light stabilizing agents and fluorescent brightening agents.

These agents can be contained in the color-forming layer. They may be contained in any layer, for example the protective layer, in the case of multi-layer structure. Particularly when an over-coating or under-coating layer is arranged above and/or below the color-forming layer, these layers can contain antioxidants and light stabilizing agents. Furthermore, antioxidants and the light stabilizing agents, if necessary, may be microcapsuled and contained in these layers.

Coloring chromogens to be used in the recording materials in accordance with the present invention may be leuco chromogens such as fluoran, phthalide, lactam, triphenyl methane, phenothiazine and spiropyran. These do not restrict chromogens to be used in the present invention. Any coloring chromogen can be used if it develops a color by contacting an acidic substance of developer. These coloring chromogens can be used on its own as well as a mixture of two or more compounds when a recording material for the color of the chromogen is produced. For example, coloring chromogens of three primary colors of red, blue and green or black-coloring chromogens are mixed to produce a recording material developing a color of true black.

Examples of fluoran chromogens are:
3-diethylamino-6-methyl-7-anilinofluoran,
3-dibutylamino-6-methyl-7-anilinofluoran,
3-(N-ethyl-N-isobutylamino)-6-methyl-7-anilinofluoran,
3-(N-methyl-N-propylamino)-6-methyl-7-anilinofluoran,
3-(N-ethyl-N-isopentylamino)-6-methyl-7-anilinofluoran,
3-diethylamino-7-(o-chloroanilino)fluoran,
3-dibutylamino-7-(o-chloroanilino)fluoran,
3-(N-ethyl-p-toluidino)-6-methyl-7-anilinofluoran,
3-(N-cyclohexyl-N-methylamino)-6-methyl-7-anilinofluoran,
3-pyrrolidino-6-methyl-7-anilinofluoran
3-piperidino-6-methyl-7-anilinofluoran
3-dimethylamino-7-(m-trifluoromethylanilino)fluoran,
3-dipentylamino-6-methyl-7-anilinofluoran,
3-(N-ethoxypropyl-N-ethylamino)-6-methyl-7-anilinofluoran,
3-dibutylamino-7-(o-fluoroanilino)fluoran,
3-diethylaminobenzo[a]fluoran,
3-dimethylamino-6-methyl-7-chlorofluoran,
3-diethylamino-5-methyl-7-dibenzylaminofluoran,
3-diethylamino-7-dibenzylaminofluoran,
3-diethylamino-5-chlorofluoran,
3-diethylamino-6-(N,N-dibenzylamino)fluoran,
3,6-dimethoxyfluoran and
2,4-dimethyl-6-(4-dimethylaminophenyl)aminofluoran.

Examples of near infrared absorbing chromogens are:
3-(4-(4-(4-anilino)-anilino)anilino-6-methyl-7-chlorofluoran,
3,3-bis(2-(4-dimethylaminophenyl)-2-(4-methoxyphenyl) vinyl)-4,5,6,7-tetrachlorophthalide and
3,6,6-tris(dimethylamino)spiro[fluorene-9,3'-phthalide].

In addition to the above, 3,3-bis(4'-diethylaminophenyl)-6-diethylaminophthalide may be added.

When a compound or a composite of this invention is used as an image stabilizing agent or when it is used together with another developer, representative examples of developers for thermal recording paper include: bisphenol compounds such as bisphenol A, 4,4'-sec-butylidene bisphenol, 4,4'-cyclohexylidene bisphenol, 2,2-dimethyl-3,3-bis(4-hydroxyphenyl) butane, 2,2'-dihydroxydiphenyl, pentamethylene-bis(4-hydroxybenzoate), 2,2-dimethyl-3,3-di(4-hydroxyphenyl)pentane and 2,2-di(4-hydroxyphenyl) hexane; bisphenol compounds containing sulfur such as 4,4'-dihydroxydiphenyl thioether, 1,7-di(4-hydroxyphenylthio)-3,5-dioxaheptane, 2,2'-bis(4-hydroxyphenylthio)diethyl ether and 4,4'-dihydroxy-3,3'-dimethyldiphenyl thioether; 4-hydroxybenzoates such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate and diphenylmethyl 4-hydroxybenzoate; metal salts of benzoic acid such as zinc benzoate and zinc 4-nitrobenzoate; salicylic acids such as 4-(2-(4-methoxyphenyloxy)ethyloxy)salicylic acid; metal salts of salicylic acid such as zinc salicylate and zinc bis[4-(octyloxycarbonylamino)-2-hydroxybenzoate]; hydroxy sulfones such as 4,4'-dihydroxydiphenyl sulfone, 2,4'-dihydroxydiphenyl sulfone, 4-hydroxy-4'-methyldiphenyl sulfone, 4-hydroxy-4'-isopropoxydiphenyl sulfone, 4-hydroxy-4'-butoxydiphenyl sulfone, 4,4'-dihydroxy-3,3'-diallyldiphenyl sulfone, 3,4-dihydroxy-4'-methyldiphenyl sulfone and 4,4'-dihydroxy-3,3',5,5'-tetrabromodiphenyl sulfone; diesters of 4-hydroxyphthalic acid such as dimethyl 4-hydroxyphthalate, dicyclohexyl 4-hydroxyphthalate and diphenyl 4-hydroxyphthalate; esters of hydroxynaphthoic acid such as 2-hydroxy-6-carboxynaphthalene; hydroxyacetophenone; p-phenylphenol; benzyl 4-hydroxyphenyl acetate, p-benzylphenol, hydroquinone monobenzyl ether; trihalomethyl sulfones such as tribromomethylphenyl sulfone; sulfonyl ureas such as 4,4'-bis(p-toluenesulfonylaminocarbonylamino) diphenylmethane; tetracyanoquinodimethanes; and 2,4-dihydroxy-2'-methoxybenzanilide.

When a compound or a composite of this invention is used as a developer or when it is used together with another image stabilizing agent, representative examples of image stabilizing agents for thermal recording paper include:
diphenyl sulfones having an epoxy linkage such as 4-benzyloxy-4'-(2-methylglycidyloxy)-diphenyl sulfone and 4,4'-diglycidyloxydiphenyl sulfone; 1,4-diglycidyloxybenzene, 4-(a-(hydroxymethyl)benzyloxy)-4'-hydroxydiphenyl sulfone, 2-propanol derivatives, salicylic acid derivatives, metal salts (particularly zinc salt) of oxynaphthoic acid derivatives, metal salts of 2,2-methylene bis(4,6-tert-butylphenyl) phosphate and other water-insoluble zinc compounds.

Examples of sensitizers are higher fatty acid amides such as amide stearate, benzamide, anilide stearate, anilide acetoacetate, thioacetoanilide, dibenzyl oxalate, di(4-methylbenzyl) oxalate, di(4-chlorobenzyl) oxalate, dimethyl phthalate, dimethyl terephthalate, dibenzyl terephthalate, dibenzyl isophthalate, bis(tert-butylphenol) compounds, diphenyl sulfone and its derivatives, diethers of 4,4'-dihydroxydiphenyl sulfone, diethers of 2,4'-dihydroxydiphenyl sulfone, 1,2-bis(phenoxy)ethane, 1,2-bis(4-methylphenoxy)ethane, 1,2-bis(3-methylphenoxy) ethane, 2-naphthol benzyl ether, diphenyl amine, carbazole, 2,3-di-m-tolylbutane, 4-benzylbiphenyl, 4,4'-dimethylbiphenyl, m-terphenyl, di-b-naphthylphenylene diamine, phenyl 1-hydroxy-naphthoate, 2-naphthylbenzyl ether, 4-methylphenyl-biphenyl ether, 2,2-bis(3,4-dimethylphenyl)ethane, 2,3,5,6-tetramethyl-4'-methyldiphenyl methane and diphenyl carbonate. Preferred sensitizers are ethers such as 1,2-bis(3-methylphenoxy) ethane and 2-naphthylbenzyl ether and aromatic hydrocarbons such as m-terphenyl, 4-benzylbiphenyl and di(4-methylbenzyl) oxalate. More preferred are diphenyl sulfone and its derivatives. Among them, diethers of 4,4'-dihydroxydiphenyl sulfone and diethers of 2,4'-dihydroxydiphenyl sulfone are particularly preferred. Their examples are 4,4'-dimethoxydiphenyl sulfone, 4,4'-diethoxydiphenyl sulfone, 4,4'-dipropoxydiphenyl sulfone, 4,4'-diisopropoxydiphenyl sulfone, 4,4'-dibutoxydiphenyl sulfone, 4,4'-diisobutoxydiphenyl sulfone, 4,4'-dipentyloxydiphenyl sulfone, 4,4'-dihexyloxydiphenyl sulfone, 2,4'-dimethoxydiphenyl sulfone, 2,4'-diethoxydiphenyl sulfone, 2,4'-dipropoxydiphenyl sulfone, 2,4'-diisopropoxydiphenyl sulfone, 2,4'-dibutoxydiphenyl sulfone, 2,4'-diisobutoxydiphenyl sulfone, 2,4'-dipentyloxydiphenyl sulfone and 2,4'-dihexyloxydiphenyl sulfone.

Examples of fillers to be used are silica, clay, kaolin, burned kaolin, talc, satin white, aluminum hydroxide, calcium carbonate, magnesium carbonate, zinc oxide, titanium oxide, barium sulfate, magnesium silicate, aluminum silicate and plastic pigments. Salts of alkaline earth metal are particularly preferred for the recording materials of this invention. More preferred are carbonates, of which calcium carbonate and magnesium carbonate are preferred. A mixing ratio of a filler is 0.1~15 parts by weight, preferably 1~10 parts by weight, to a part by weight of a coloring chromogen. It is possible to mix other fillers to those mentioned above.

Examples of dispersing agents are sulfosuccinates such as dioctyl sodium sulfosuccinate, sodium dodecylbenzene sulfonate, sodium salts of lauryl alcohol sulfates and salts of fatty acids.

Examples of antioxidants are 2,2'-methylenebis(4-methyl-6-tert-butylphenol), 2,2'-methylenebis(4-ethyl-6-tert-butylphenol), 4,4'-propylmethylenebis(3-methyl-6-tert-butylphenol), 4,4'-butylidenebis(3-methyl-6-tert-butylphenol), 4,4'-thiobis(2-tert-butyl-5-methylphenol), 1,1,3-tris(2-methyl-4-hydroxy-5-tert-butylphenyl)butane, 1,1,3-tris(2-methyl-4-hydroxy-5-cyclohexylphenyl)butane and 4-[4-[1,1-bis(4-hydroxyphenyl) ethyl]-α,α'-dimethylbenzyl]phenol.

Examples of desensitizers are aliphatic higher alcohols, polyethylene glycol and guanidine derivatives.

Examples of antitack agents are stearic acid, zinc stearate, calcium stearate, carnauba wax, paraffin wax and ester wax.

Examples of light stabilizing agents may include UV radiation absorbing agents of salicylic acid compounds such as phenylsalicylate, p-tert-butylphenylsalicylate and p-octylphenylsalicylate; UV radiation absorbing agents of benzophenone compounds such as 2,4-dihydorxybenzophenone, 2-hydroxy-4-methoxybenzophenone, 2-hydroxy-4-benzyloxybenzophenone, 2-hydroxy-4-octyloxybenzophenone, 2-hydroxy-4-dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone and bis(2-methoxy-4-hydroxy-5-benzoylphenyl)methane; UV radiation absorbing agents of benzotriazol compounds such as 2-(2'-hydroxy-5'-methylphenyl)benzotriazole, 2-(2'-hydroxy-5'-tert-butylphenyl)benzotriazole, 2-(2'-hydroxy-3',5'-di-tert-butylphenyl)benzotriazole, 2-(2'-hydroxy-3'-tert-butyl-5'-methylphenyl)-5-chlorobenzotriazole, 2-(2'-hydroxy-3',5'-di-tert-butylphenyl)-5-chlorobenzotriazole, 2-(2'-hydroxy-3',5'-di-tert-amylphenyl)benzotriazole, 2-[2'-hydroxy-3'-(3",4",5",6"-tetrahydrophthalimidemethyl)-5'-methylphenyl] benzotriazole, 2-(2'-hydroxy-5'-tert-octylphenyl) benzotriazole, 2-[2'-hydroxy-3',5'-bis(a,a-dimethylbenzyl) phenyl]-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1"-ethyloctyl)oxyphenyl]benzotriazole, 2-[2'-hydroxy-4'-(1"-propyloctyl)oxyphenyl]benzotriazole, 2-[2'-hydroxy-4'-(1"-propylheptyl)oxyphenyl]benzotriazole, 2-[2'-hydroxy-4'-(1"-propylhexyl)oxyphenyl]benzotriazole, 2,2'-methylenebis[4-(1,1,3,3-tetramethylbutyl)-6-(2H-benzotriazol-2-yl)]phenol and the condensate of polyethylene glycol and methyl-3-[3-tert-butyl-5-(2H-benzotriazol-2-yl)-4-hydroxyphenyl]propionate; UV radiation absorbing agents of cyanoacrylate compounds such as 2'-ethylhexyl-2-cyano-3,3-diphenylacrylate and ethyl-2-cyano-3,3-diphenylacrylate; UV radiation absorbing agents of hindered amine compounds such as bis(2,2,6,6-tetramethyl-4-piperidyl sebacate, bis(2,2,6,6-tetramethyl-4-piperidyl) succinate and bis(1,2,2,6,6-pentamethyl-4-piperidyl) 2-(3,5-di-tert-butyl)malonate; and 1,8-dihydroxy-2-acetyl-3-methyl-6-methoxynaphthalene and its related compounds.

Examples of fluorescent dyes may include the following:

Disodium 4,4'-bis[2-anilino-4-(2-hydroxyethyl)amino-1,3,5-triazinyl-6-amino]stilbene-2,2'-disulfonate, Disodium 4,4'-bis[2-anilino-4-bis(hydroxyethyl)amino-1,3,5-triazinyl-6-amino]stilbene-2,2'-disulfonate, Disodium 4,4'-bis[2-methoxy-4-(2-hydroxyethyl)amino-1,3,5-triazinyl-6-amino]stilbene-2,2'-disulfonate, Disodium 4,4'-bis[2-methoxy-4-(2-hydroxypropyl)amino-1,3,5-triazinyl-6-amino]stilbene-2,2'-disulfonate, Disodium 4,4'-bis[2-m-sulfoanilino-4-bis(hydroxyethyl) amino-1,3,5-triazinyl-6-amino]stilbene-2,2'-disulfonate, Tetrasodium 4-[2-p-sulfoanilino-4-bis(hydroxyethyl)amino-1,3,5-triazinyl- 6-amino]-4'-[2-m-sulfoanilino-4-bis (hydroxyethyl)amino-1,3,5-triazinyl-6-amino]stilbene-2,2'-disulfonate, Tetrasodium 4,4'-bis[2-p-sulfoanilino-4-bis(hydroxyethyl) amino-1,3,5-triazinyl-6-amino]stilbene-2,2'-disulfonate, Hexasodium 4,4'-bis[2-(2,5-disulfoanilino)-4-phenoxyamino-1,3,5-triazinyl-6-amino]stilbene-2,2'-disulfonate, Hexasodium 4,4'-bis[2-(2,5-disulfoanilino)-4-(p-methoxycarbonylphenoxy)amino-1,3,5-triazinyl-6-amino]stilbene-2,2'-disulfonate, Tetrasodium 4,4'-bis[2-(p-sulfophenoxy)-4-bis (hydroxyethyl)amino-1,3,5-triazinyl-6-amino]stilbene-2,2'-disulfonate, Hexasodium 4,4'-bis[2-(2,5-disulfoanilino)-4-formalinylamino-1,3,5-triazinyl-6-amino]stilbene-2,2'-disulfonate and Hexasodium 4,4'-bis[2-(2,5-disulfoanilino)-4-bis (hydroxyethyl)amino-1,3,5-triazinyl-6-amino]stilbene-2,2'-disulfonate.

The compounds or composite of this invention can be used for producing carbonless paper in the similar manner to known image stabilizing agents, developers or sensitizers. For example, a coloring chromogen is microcapsuled by a known method, dispersed with a proper dispersing agent and applied onto paper to produce a coloring-agent sheet. Or a dispersion of a developer is applied onto paper to produce a developer sheet. When doing so, a compound of this invention can be dispersed in a dispersion either for the coloring-agent sheet or developer sheet when it is used as an image stabilizing agent. Two sheets thus produced are combined to form carbonless paper. The carbonless paper can be of a unit structure consisting of an upper-side paper, of which microcapsules encapsuling an organic solvent solution of a coloring chromogen are applied on the back surface, and an under-side paper, of which a developer (acidic substance) is applied on the upper surface. It can be also so-called self-content paper of which microcapsules and a developer are coated onto the same surface of paper.

Known developers, alone or mixed with a compound of this invention, can be used to produce the paper mentioned above. Examples include inorganic acidic substances such as acid clay, activated clay, attapulgite, bentonite, colloidal silica, aluminum silicate, magnesium silicate, zinc silicate, tin silicate, burned kaolin and talc; aliphatic carboxylic acids such as oxalic acid, maleic acid, tartaric acid, citric acid, succinic acid and stearic acid; aromatic carboxylic acids such as benzoic acid, p-tert-butylbenzic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid, 3-phenyl-5-(2,2-dimethylbenzyl)salicylic acid, 3,5-di-(2-methylbenzyl)salicylic acid and 2-hydroxy-1-benzyl-3-naphthoic acid; metal salts of these aromatic carboxylic acids such as zinc, magnesium, aluminum and titanium; developers of phenol resins such as p-phenylphenol-formalin resin and p-butylphenol-acetylene resin; and mixtures of the phenol resin developers and the above-mentioned metal salts of aromatic carboxylic acids.

Recording materials of the present invention are described in detail with examples, but not restricted to them.

EXAMPLE 11

Production of Thermal Recording Paper

| Chromogen dispersion (Liquid A) | |
| --- | --- |
| 2-anilino-3-methyl-6-dibutylaminofluoran | 7.0 g |
| 15% aqueous solution of polyvinyl alcohol | 30.0 g |
| Filler (calcium carbonate) | 13.5 g |
| Pure water | 49.5 g |
| Developer dispersion (Liquid B) | |
| 4,4'-bis[4-[4-(4-hydroxyphenylsulfonyl) phenoxy]-2-trans-butenyloxy]di phenyl sulfone (Compound No. 1-1) | 7.0 g |
| 15% aqueous solution of polyvinyl alcohol | 30.0 g |
| Filler (calcium carbonate) | 13.5 g |
| Pure water | 49.5 g |
| Filler dispersion (Liquid C) | |
| 15% aqueous solution of polyvinyl alcohol | 30.0 g |
| Filler (calcium carbonate) | 20.5 g |
| Pure water | 49.5 g |

Each of the mixture of the above composition was ground by a sand grinder sufficiently. The dispersion of each of Liquids A, B and C was prepared. A part by weight of Liquid A, 2 parts by weight of Liquid B and a part by weight of Liquid C were mixed to prepare a coating solution. This solution was applied onto a plain paper with a wire rod (No. 12) and dried. The paper was subjected to calendaring to give a thermal recording paper. (A coating amount was approximately 5.5 g/m2 by weight of the dried.)

COMPARISON EXAMPLE 1

Example 11 was repeated to prepare a thermal recording paper except that 4-isopropoxy-4'-hydroxydiphenyl sulfone was used instead of the compound of this invention in the developer dispersion of Example 11.

EXAMPLE 12

Example 11 was repeated to prepare a thermal recording paper except that 4,4'-bis[4-(4-hydroxyphenylsulfonyl) phenoxy-4-butyloxy]diphenyl sulfone (Compound No. 1-2) was used instead of Compound No. 1-1 of this invention in the developer dispersion of Example 11.

EXAMPLE 13

Example 11 was repeated to prepare a thermal recording paper except that 4-isopropoxy-4'-hydroxydiphenyl sulfone was used instead of the compound of this invention in the developer dispersion of Example 11 and the composition of the filler dispersion (Liquid C) was changed to the following:

| 4,4'-bis[4-[4-(4-hydroxyphenylsulfonyl)phenoxy-2-trans-butenyloxy]diphenyl sulfone (Compound No. 1-1) | 7.0 g |
| --- | --- |
| 15% aqueous solution of polyvinyl alcohol | 30.0 g |
| Filler (clay) | 13.5 g |
| Pure water | 49.5 g |

EXAMPLE 14

Example 13 was repeated to prepare a thermal recording paper except that 1,4-bis-4-[4-[4-(4-hydroxyphenylsulfonyl)phenoxy-2-trans-butenyloxy]phenylsulfonyl]phenoxy-cis-2-butene (Compound No. 1-13) was used instead of Compound No. 1-1 in the filler dispersion (Liquid C).

EXAMPLE 15

Example 11 was repeated to prepare a thermal recording paper except that 1,4-bis[4-(4-hydroxyphenylsulfonyl) phenoxy]-2-butene (trans) was used instead of the compound of this invention in the developer dispersion of Example 11 and the composition of the filler dispersion (Liquid C) was changed to the following:

| 4,4'-bis[4-[4-(4-hydroxyphenylsulfonyl)phenoxy-2-trans-butenyloxy]diphenyl sulfone (Compound No. 1-1) | 7.0 g |
| --- | --- |
| 15% aqueous solution of polyvinyl alcohol | 30.0 g |
| Filler (clay) | 13.5 g |
| Pure water | 49.5 g |

EXAMPLE 16

| Chromogen dispersion (Liquid A) | |
| --- | --- |
| 2-anilino-3-methyl-6-dibutylaminofluoran | 20.0 g |
| 10% aqueous solution of polyvinyl alcohol | 105.0 g |
| Developer dispersion (Liquid B) | |
| 4,4'-bis[4-(4-hydro xyphenylsulfonyl)phenoxy-2-ethyleneoxyethoxy] diphenyl sulfone (Compound No. 1-17) | 20.0 g |
| 10% aqueous solution of polyvinyl alcohol | 105.0 g |
| Filler dispersion (Liquid C) | |
| bis(4-methylbenzyl) oxalate | 20.0 g |
| 10% aqueous solution of polyvinyl alcohol | 105.0 g |
| Filler dispersion (Liquid D) | |
| 10% aqueous solution of polyvinyl alcohol | 26.2 g |
| Filler (calcium carbonate) | 27.8 g |
| Pure water | 71.0 g |

Each of the mixture of the above composition was ground by a sand grinder sufficiently. The dispersion of each of Liquids A, B, C and D was prepared. A part by weight of Liquid A, 2 parts by weight of Liquid B, a part by weight of Liquid C, 4 parts by weight of Liquid D and 0.5 parts by weight of a dispersion of zinc stearate (Hydrin Z-7-30, Chukyo Yushi Co.) were mixed to prepare a coating solution. This solution was applied onto a plain paper with a wire rod (No. 12) and dried. The paper was subjected to calendaring to give a thermal recording paper. (A coating amount was approximately 5.5 g/m2 by weight of the dried.)

EXAMPLE 17

Example 16 was repeated to prepare a thermal recording paper except that 2,2'-bis[4-(4-hydroxyphenylsulfonyl)

phenoxy]diethyl ether containing 8.4% by weight of 4,4'-bis[4-(4-hydroxyphenylsulfonyl)phenoxy-2-ethyleneoxyethoxy]diphenyl sulfone was used instead of 4,4'-bis[4-(4-hydroxyphenylsulfonyl)phenoxy-2-ethyleneoxyethoxy]diphenyl sulfone in Liquid B of Example 16.

EXAMPLE 18

Example 16 was repeated to prepare a thermal recording paper except that 2,2'-bis[4-(4-hydroxyphenylsulfonyl) phenoxy]diethyl ether containing 24% by weight of 4,4'-bis [4-(4-hydroxyphenylsulfonyl)phenoxy-2-ethyleneoxyethoxy]diphenyl sulfone and 6% by weight of 2,2'-bis[4-[4-[4-(4-hydroxyphenylsulfonyl)phenoxy-2-ethyleneoxyethoxy]phenylsulfonyl]phenoxy]diethyl ether (Compound No. 1-21) was used instead of 4,4'-bis[4-(4-hydroxyphenylsulfonyl)phenoxy-2-ethyleneoxyethoxy] diphenyl sulfone in Liquid B of Example 16.

EXAMPLE 19

Example 16 was repeated to prepare a thermal recording paper except that a composite synthesized in Example 6 was used instead of 4,4-bis[4-(4-hydroxyphenylsulfonyl) phenoxy-2-ethyleneoxyethoxy]diphenyl sulfone in Liquid B of Example 16.

EXAMPLE 20

Example 16 was repeated to prepare a thermal recording paper except that α,α'-bis[4-(4-hydroxyphenylsulfonyl) phenoxy]-p-xylene containing 23% by weight of 4,4'-bis[4-(4-hydroxyphenylsulfonyl)phenyl-1,4-phenylenebismethyleneoxy]diphenyl sulfone (Compound No. 1-18) and 11% by weight of α,α'-bis[4-[4-[4-(4-hydroxyphenylsulfonyl)phenyl-1,4-phenylenebismethyeneoxy]phenylsulfonyl]phenoxy]-p-xylene (Compound No. 1-22) was used instead of 4,4'-bis [4-(4-hydroxyphenylsulfonyl)phenoxy-2-ethyleneoxyethoxy]diphenyl sulfone in Liquid B of Example 16.

COMPARISON EXAMPLE 2

Example 16 was repeated to prepare a thermal recording paper except that 2,2'-bis[4-(4-hydroxyphenylsulfonyl) phenoxy]diethyl ether was used instead of 4,4'-bis[4-(4-hydroxyphenylsulfonyl)phenoxy-2-ethyleneoxyethoxy] diphenyl sulfone in Liquid B of Example 16.

COMPARISON EXAMPLE 3

Example 16 was repeated to prepare a thermal recording paper except that α,α'-bis[4-(4-hydroxyphenylsulfonyl) phenoxy]-p-xylene was used instead of 4,4'-bis[4-(4-hydroxyphenylsulfonyl)phenoxy-2-ethyleneoxyethoxy] diphenyl sulfone in Liquid B of Example 16.

TEST EXAMPLE 1

Testing of Plasticizer Resistance of Thermal Recording Paper

Each of the thermal recording papers prepared in Examples 11 to 20 and Comparison Examples 1 to 3 was developed for a color in checkered pattern at a printing voltage of 26V and pulse width of 1.8 ms by a tester for developing a color on thermal recording paper (Okura Denki Co., TH-PMD). The colored surface was tightly covered with wrapping film of vinyl chloride. The papers were tested for plasticizer resistance for 32 hours at 40° C. The color densities before and after the test were measured by Macbeth reflection densitometer (filter used: #106). The results are shown in Table 1.

TABLE 1

(Plasticizer Resistance Tests)

| Example | Color density (before) | Color density (after) | Remaining rate (%) |
| --- | --- | --- | --- |
| 11 | 0.59 | 0.38 | 62 |
| 12 | 0.42 | 0.30 | 71 |
| 13 | 1.23 | 0.43 | 35 |
| 14 | 1.20 | 0.48 | 40 |
| 15 | 1.01 | 0.73 | 72 |
| 16 | 1.17 | 1.08 | 92 |
| 17 | 1.16 | 0.76 | 66 |
| 18 | 1.20 | 1.02 | 85 |
| 19 | 1.12 | 1.11 | 99 |
| 20 | 1.09 | 0.80 | 73 |
| Comparison 1 | 1.16 | 0.08 | 7 |
| Comparison 2 | 1.16 | 0.16 | 22 |
| Comparison 3 | 1.22 | 0.24 | 20 |

$$\text{Remaining ratio} = \frac{\text{Color density (after test)}}{\text{Color density (before test)}} \times 100$$

The greater the measured value in Table 1 is, the higher the color density. A larger value of the remaining ratio means less color fading.

TEST EXAMPLE 2

Testing of Oil Resistance of Thermal Recording Paper

Each of the thermal recording papers prepared in Examples 16 to 20 and Comparison Examples 2 and 3 was developed for a color in the same way as that in Test Example 1. The papers with colored images were immersed in salad oil at 25° C. for 8 days in order to test the oil resistance. The optical densities of the images before and after the test were measured by Macbeth reflection densitometer RD-514 (filter used: #106). The results are shown in Table 2.

TABLE 2

(Oil Resistance Tests)

| Example | Color density (beforer) | Color density (after) | Remaining rate (%) |
| --- | --- | --- | --- |
| Example 16 | 1.15 | 1.14 | 99 |
| Example 17 | 1.18 | 0.93 | 79 |
| Example 18 | 1.20 | 1.13 | 94 |
| Example 19 | 1.12 | 1.11 | 99 |
| Example 20 | 1.08 | 0.90 | 83 |
| Comparison 2 | 1.17 | 0.30 | 26 |
| Comparison 3 | 1.25 | 0.48 | 24 |

The greater the measured value in Table 2 is, the higher the color density. A larger value of the remaining ratio means less color fading.

TEST EXAMPLE 3

Testing of Water Resistance of Thermal Recording Paper

Each of the thermal recording papers prepared in Examples 18, 19 and 20 and Comparison Example 1 was developed for a color in the same way as that in Test Example 1. The papers with colored images were immersed in pure water at 25° C. for 3 days. The test pieces were dried at 50° C. for 3 minutes. The optical densities of the images were measured. The results are shown in Table 3.

TABLE 3

(Water Resistance Tests)

| Example | Color density (beforer) | Color density (after) | Remaining rate (%) |
|---|---|---|---|
| Example 18 | 1.20 | 1.10 | 92 |
| Example 19 | 1.12 | 1.11 | 99 |
| Example 20 | 1.08 | 1.03 | 95 |
| Comparison 1 | 1.16 | 0.67 | 58 |

Industrial Use of the Invention

The recording materials containing the diphenyl sulfone crosslinking compounds or composites of the present invention are excellent in the preservability of colored images, particularly in oil resistance and plasticizer resistance. The water resistance is also good.

What is claimed is:

1. Diphenyl sulfone crosslinking compounds represented by general formula (I):

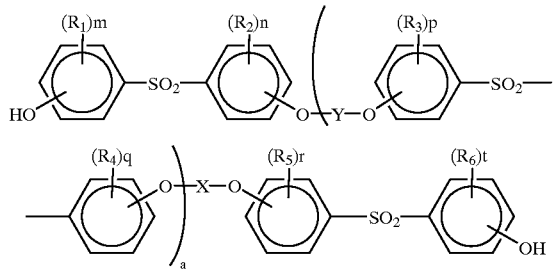

wherein X and Y are, same or different, a straight-chain or branched, saturated or unsaturated $C_1$–$C_{12}$ hydrocarbon group which may have an ether linkage, or

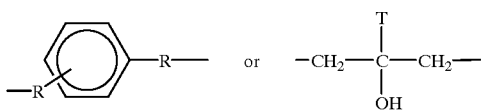

wherein

R is methylene or ethylene and T is hydrogen or an alkyl group having 1 to 4 carbons;

$R_1$–$R_6$ are each independently halogen, an alkyl group having 1 to 6 carbons, or an alkenyl group; m, n, p, q, r, t are 0 or an integer between 1 and 4 and, when more than 2, $R_1$–$R_6$ may be different; and a is an integer between 1~10.

2. Composition containing at least one of the diphenyl sulfone crosslinking compounds represented by general formula (I) according to claim 1 and at least one of diphenyl sulfone derivatives represented by general formula (II)

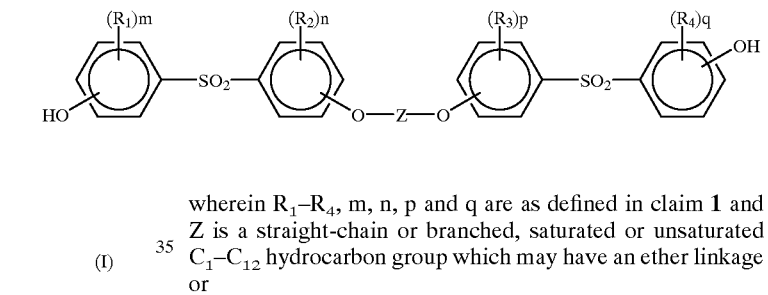

wherein $R_1$–$R_4$, m, n, p and q are as defined in claim 1 and Z is a straight-chain or branched, saturated or unsaturated $C_1$–$C_{12}$ hydrocarbon group which may have an ether linkage or

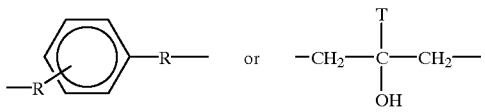

wherein R is methylene or ethylene and T is hydrogen or an alkyl group having 1 to 4 carbons.

3. Composition according to claim 2 in which the total amount of the diphenyl sulfone crosslinking compounds represented by general formula (I) is 0.05 to 99% by weight.

4. Recording materials containing coloring chromogens and at least one of the diphenyl sulfone crosslinking compounds according to claim 1 on a support.

5. Recording materials containing coloring chromogens and at least one of the diphenyl sulfone crosslinking compounds represented by general formula (I) according to claim 1 and at least one of diphenyl sulfone derivatives represented by general formula (II)

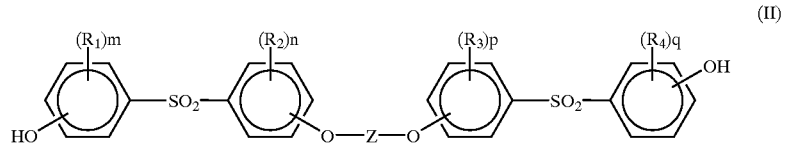

wherein $R_1$–$R_4$, m, n, p and q are as defined in claim 1 and Z is a straight-chain or branched, saturated or unsaturated $C_1$–$C_{12}$ hydrocarbon group which may have an ether linkage or
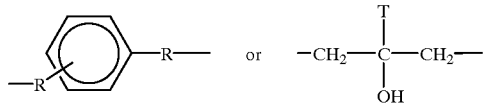
wherein R is methylene or ethylene and T is hydrogen or an alkyl group having 1 to 4 carbons on a support.
* * * * *